United States Patent
Clemens et al.

(10) Patent No.: US 8,041,434 B2
(45) Date of Patent: Oct. 18, 2011

(54) IMPLANTABLE MEDICAL ELECTRICAL LEAD BODIES PROVIDING IMPROVED ELECTRODE CONTACT

(75) Inventors: William J. Clemens, Fridley, MN (US); Nicole L. Werner, Cleveland Heights, OH (US); Deborah A. Loch, Saint Paul, MN (US); Douglas Stephen Hine, Forest Lake, MN (US); Douglas N. Hess, Maple Grove, MN (US); Carla C. Pfeiffer, Anoka, MN (US); Walton William Baxter, III, San Clemente, CA (US)

(73) Assignee: Medtronic, Inc., Minneapolis, MN (US)

( * ) Notice: Subject to any disclaimer, the term of this patent is extended or adjusted under 35 U.S.C. 154(b) by 286 days.

(21) Appl. No.: 12/413,176

(22) Filed: Mar. 27, 2009

(65) Prior Publication Data
US 2009/0248127 A1    Oct. 1, 2009

Related U.S. Application Data (60) Provisional application No. 61/040,454, filed on Mar. 28, 2008.

(51) Int. Cl.
*A61N 1/00*    (2006.01)
(52) U.S. Cl. ...................................................... 607/122
(58) Field of Classification Search ................ 607/40, 607/122
See application file for complete search history.

(56) References Cited

U.S. PATENT DOCUMENTS

| | | | |
|---|---|---|---|
| 5,423,772 A | 6/1995 | Lurie et al. | |
| 5,683,445 A | 11/1997 | Swoyer | |
| 5,995,876 A | 11/1999 | Kruse et al. | |
| 5,999,858 A | 12/1999 | Sommer et al. | |
| 6,006,139 A | 12/1999 | Kruse et al. | |
| 6,144,882 A | 11/2000 | Sommer et al. | |
| 6,192,280 B1 | 2/2001 | Sommer et al. | |
| 6,556,873 B1 * | 4/2003 | Smits | 607/122 |
| 6,871,085 B2 | 3/2005 | Sommer | |
| 7,031,777 B2 | 4/2006 | Hine et al. | |
| 7,107,105 B2 | 9/2006 | Bjorklund et al. | |
| 2009/0264974 A1 * | 10/2009 | Zhang et al. | 607/122 |

FOREIGN PATENT DOCUMENTS
WO    0053255    9/2000

OTHER PUBLICATIONS

Fusheng You et al., "A Quantitative Method Based on Total Relative Change for Dynamic Electrical Impedance Tomography", *IEEE Transactions on Biomedical Engineering*, vol. 55, No. 3, Mar. 2008, pp. 1224-1220. Shantanu Sarker et al., "A Detector for a Chronic Implantable Atrial Tachyarrhythmia Monitor", *IEEE Transactions on Biomedical Engineering*, vol. 55, No. 3, Mar. 2008, pp. 1219-1224.
International Search Report, PCT/US2009/038720, 3 pages.

* cited by examiner

*Primary Examiner* — George Manuel
*Assistant Examiner* — Robert Wieland
(74) *Attorney, Agent, or Firm* — Reed A. Duthler (57) ABSTRACT

A distal section of an implantable medical electrical lead body includes a pair of pre-formed arcuate segments between which an approximately straight segment extends. The approximately straight segment includes a first portion extending distally from a first of the pair pre-formed arcuate segments, a second portion extending from the first portion, a third portion extending from the second to a second of the pair pre-formed arcuate segments. An electrode is coupled to the second portion of the approximately straight segment, and the adjacent first portion has a stiffness which is less than that of the first of the pair pre-formed arcuate segments and preferably less than the stiffness of the third portion, so that, when the distal section of the lead body is implanted, for example, within a cardiac vein, the lead buckles to bring the electrode into closer contact with surrounding tissue.

20 Claims, 6 Drawing Sheets

Fig. 3B ered within an outer insulative sheath 103, for example, formed

IMPLANTABLE MEDICAL ELECTRICAL LEAD BODIES PROVIDING IMPROVED ELECTRODE CONTACT

CROSS-REFERENCE TO RELATED APPLICATIONS

This application claims the benefit of U.S. Provisional Application No. 61/040,454, filed on Mar. 28, 2008. The disclosure of the above application is incorporated herein by reference.

TECHNICAL FIELD

The present invention pertains to implantable medical electrical leads and more particularly to lead body construction.

BACKGROUND

In order to safely and effectively provide electrical stimulation to the left side of a heart, medical electrical leads have been designed for implantation within the coronary venous vasculature. Some of the challenges associated with implanting a lead within a coronary vein include the navigation of one or more electrodes of the lead to particular implant sites and, upon reaching the desired site(s), fixation of the lead to maintain stable stimulation and/or sensing via the electrode(s) thereof. A variety of lead body designs have been proposed to address these challenges, but there is still a need for lead body designs that can further facilitate the positioning of one or more lead electrodes in good electrical contact with surrounding tissue at a variety of sites within the coronary venous vasculature across a population of patients.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1A:
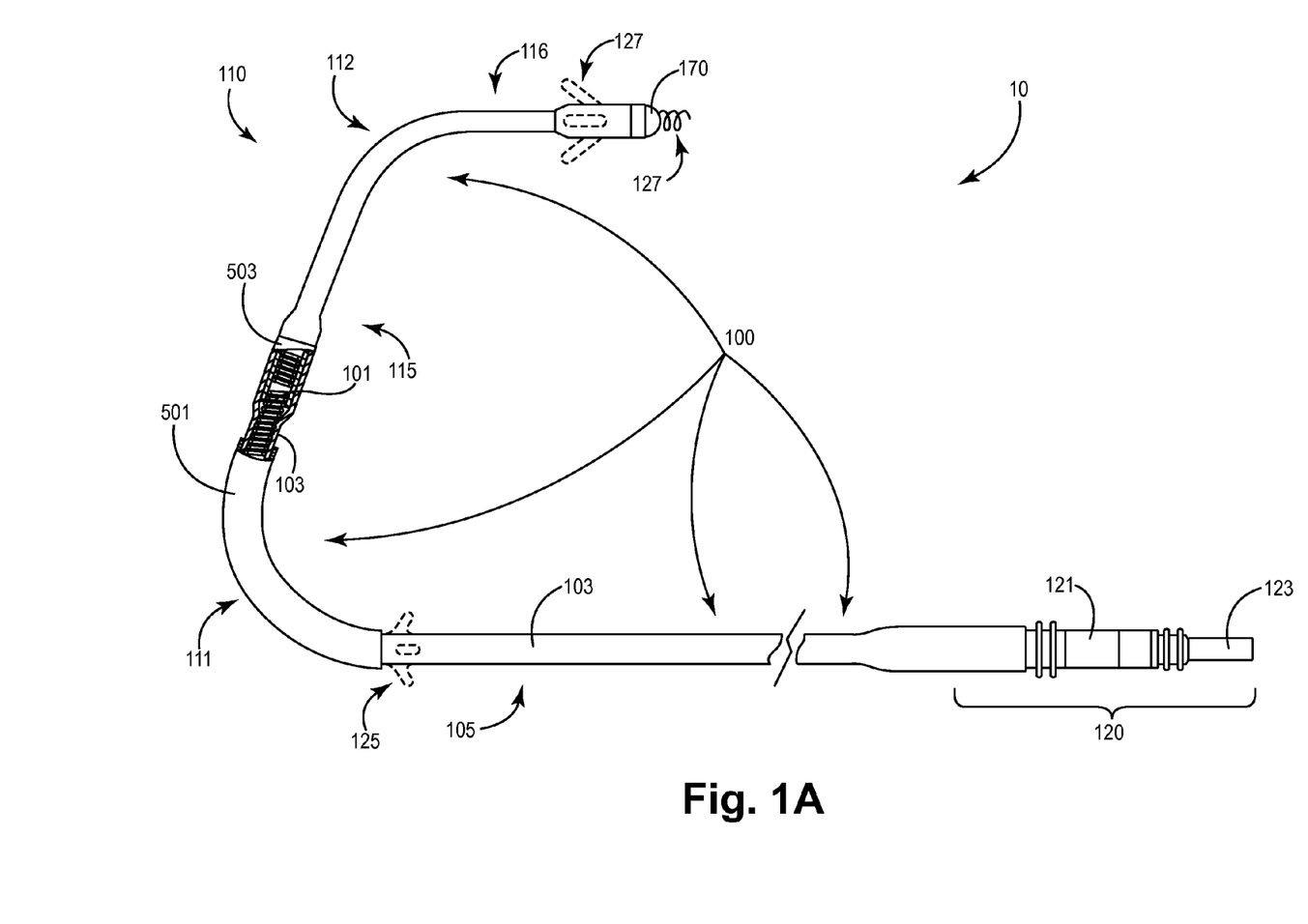
FIG. 1A is a plan view of an implantable medical electrical lead, according to some embodiments of the present invention.

FIG. 1A is a plan view of an implantable medical electrical lead 10, according to some embodiments of the present invention. FIG. 1A illustrates lead 10 including a proximal connector terminal 120, for example, conforming to the IS-1 standard, which is known to those skilled in the art, an elongate lead body 100 extending distally from connector terminal 120, and a pair of electrodes 503, 170, which are coupled to lead body 100.

According to the illustrated embodiment, lead body 100 is formed by a multi-conductor conductor coil 101 extending within an outer insulative sheath 103, for example, formed from medical grade silicone or polyurethane; coil 101 includes a plurality of filars, for example, formed from MP35N wire, at least one of which electrically couples electrode 503 to a contact ring 121 of connector terminal 120 and at least one other of which couples distal tip electrode 170 to a contact pin 123 of connector terminal 120. Those skilled in the art will appreciate that the at least one filar of coil 101 that couples electrode 503 is electrically isolated from the at least one other filar of coil 101 that couples distal tip electrode 170, and that the electrical isolation my be provided by a insulative jacket, for example, formed from SI polyimide, which extends around one or both of the filars. Those skilled in the art will further appreciate that lead bodies of the present invention may be formed with a variety of alternative conductor configurations, one example of which includes cabled conductors extending within separate lumens of a multilumen insulative sheath. According to exemplary embodiments of the present invention, lead body 100 has an outer diameter ranging between approximately 0.05 inch (4F) and approximately 0.09 inch (7F). Those skilled in the art are familiar with various methods for delivering electrodes 503, 170 to an implant site, for example, using accessories such as stylets, guide wires and/or catheters; and, it should be noted that embodiments of the present invention are not limited by any particular features accommodating any particular type of delivery method.

FIG. 1A further illustrates lead body 100 including an approximately straight proximal section 105, which extends distally from connector terminal 120, and a distal section 110, which extends distally from proximal section 105. According to the illustrated embodiment distal section 110 includes a pair of pre-formed arcuate segments 111, 112, respectively, between which an approximately straight segment 115 extends, and an approximately straight segment 116 extending distally from pre-formed arcuate segment 112. With reference to FIG. 1A, it should be understood that distal section 110 of lead body 100 is shown in an as-formed relaxed state and that distal section 110 is flexible to bend, for insertion within a delivery catheter, and to somewhat conform with a curvature of a vessel in which lead 10 may be implanted. Either or both of insulative sheath 103 and conductor coil 101 may be set into the pre-formed shape illustrated for distal section 110, according to methods known to those skilled in the art; according to some preferred embodiments, outer insulative sheath 103 is formed from a polyurethane having a durometer of approximately 55D and being heat set into the curvature necessary to provide the illustrated pre-formed shape for distal section 110. According to other embodiments in which coil 101 is set into the pre-formed shape, the shape may be more resistant to relaxation in the relatively warm environment of the venous system. Although FIG. 1A illustrates each of segments 111, 112, 115, 116 of distal section 110 extending approximately co-planar with one another and with proximal section 105, it should be understood that the invention is not so limited, and, according to alternate embodiments, any of the segments may extend out of plane with respect to any of the other segments and/or with respect to proximal section 105.

According to the illustrated embodiment, the pre-formed shape of distal section 110 facilitates positioning of lead 10 in a coronary vein that extends distally from the coronary sinus around the left side of the heart, and may further facilitate fixation of lead 10 so that distal tip electrode 170 can make stable contact with surrounding tissue to pace the left side of the heart. Electrode 503 may function in concert with distal tip electrode 170 for bipolar sensing, but, according to some preferred embodiments, electrode 503 functions as an alternative pacing electrode to distal tip electrode 170, when tip electrode 170 cannot be positioned to provide effective left ventricular pacing. Those skilled in the art understand the difficulties often associated with properly positioning an electrode for left ventricular pacing, which difficulties may be due to a particular coronary venous anatomy and/or a particular myocardial conduction characteristic, for example, caused by ischemia, that prevents the myocardium from effectively responding to pacing at a particular site.

FIG. 1A further illustrates, with dashed lines, various optional fixation members 125, 127, which lead 10 may include, if additional fixation is desired. Member 125 would be attached to proximal section 105, at a location in proximity to pre-formed arcuate segment 111, where protrusions thereof may contact a surrounding coronary vein wall, for example, that of a coronary sinus; an example of such a fixation member having deployable protrusions is described in commonly assigned U.S. Pat. No. 7,107,105, which is hereby incorporated by reference. One of members 127, either tines or a helical barb, both of which are well known to those skilled in the art, would be attached to distal section 110, in proximity to electrode 170. It should be noted that embodiments of the present invention are not limited by the presence or absence of a fixation member or by the type thereof, if present, and any type of active or passive fixation member that is known to those skilled in the art may be employed.

Figure 1B:
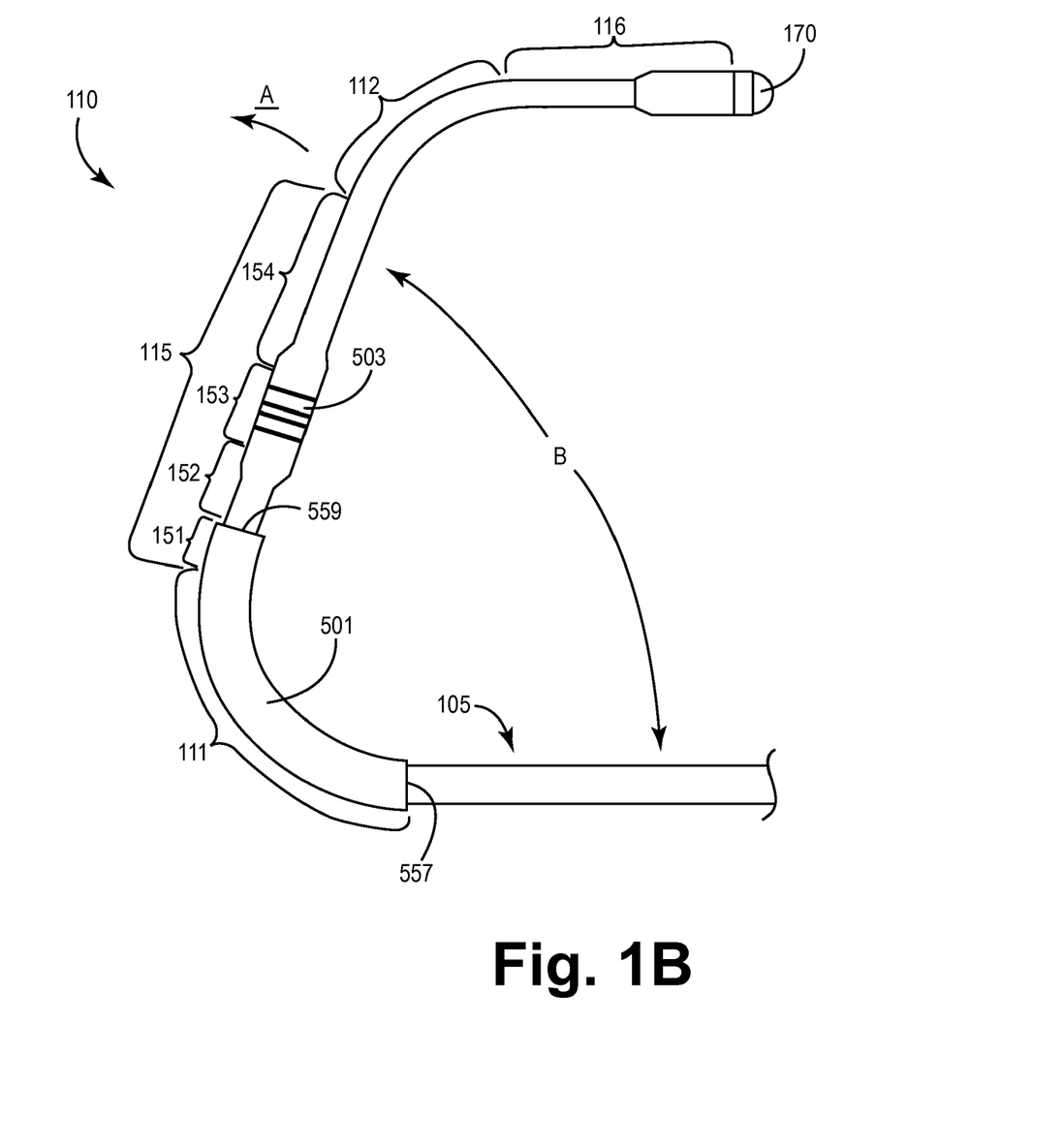
FIG. 1B is an enlarged view of a distal section of the lead shown in FIG. 1A, according to some embodiments, wherein the distal section is in a relaxed state.

Turning now to FIG. 1B, which is an enlarged view of distal section 110, according to some embodiments, further detail concerning segments 111 and 115 will be described. FIG. 1B illustrates pre-formed arcuate segment 111 extending from proximal section 105 in a bend such that approximately straight distal segment 115 extends from pre-formed arcuate segment 111 at an angle β with respect to proximal section 105, angle β being enclosed between proximal section 105 and segment 115. According to some preferred embodiments, angle β is between approximately 45 degrees and approximately 90 degrees. FIG. 1B further illustrates approximately straight distal segment 115 including a portion 151 extending distally from pre-formed arcuate segment 111, a portion 152 extending distally from portion 151, a portion 153 extending distally from portion 152, and a portion 154 extending distally from portion 153 to pre-formed arcuate segment 112, which bends toward connector terminal 120.

According to the illustrated embodiment, electrode 503 is coupled to portion 153 of segment 115. The arcuate segments 111 and 112, as well as portions 151, 152, 153 and 154 are free of electrodes. Portion 152 has a stiffness that is less than a stiffness of arcuate segment 111 and less than a stiffness of portion 153. As is illustrated in FIG. 1B, when the lead is inserted into the coronary sinus and, such that arcuate segment 111 bears against the wall of a coronary sinus or other coronary vein, opening its curvature "B", segment 115 is deflected, per arrow A, so that portion 152 of segment 115 will preferentially bend, allowing portion 153, carrying electrode 503 to better contact the inner wall of the coronary vein. Better contact with the inner wall of the coronary vein can reduce the stimulation threshold of the pacing pulses which are thereafter applied using the electrode.

Figure 1C:
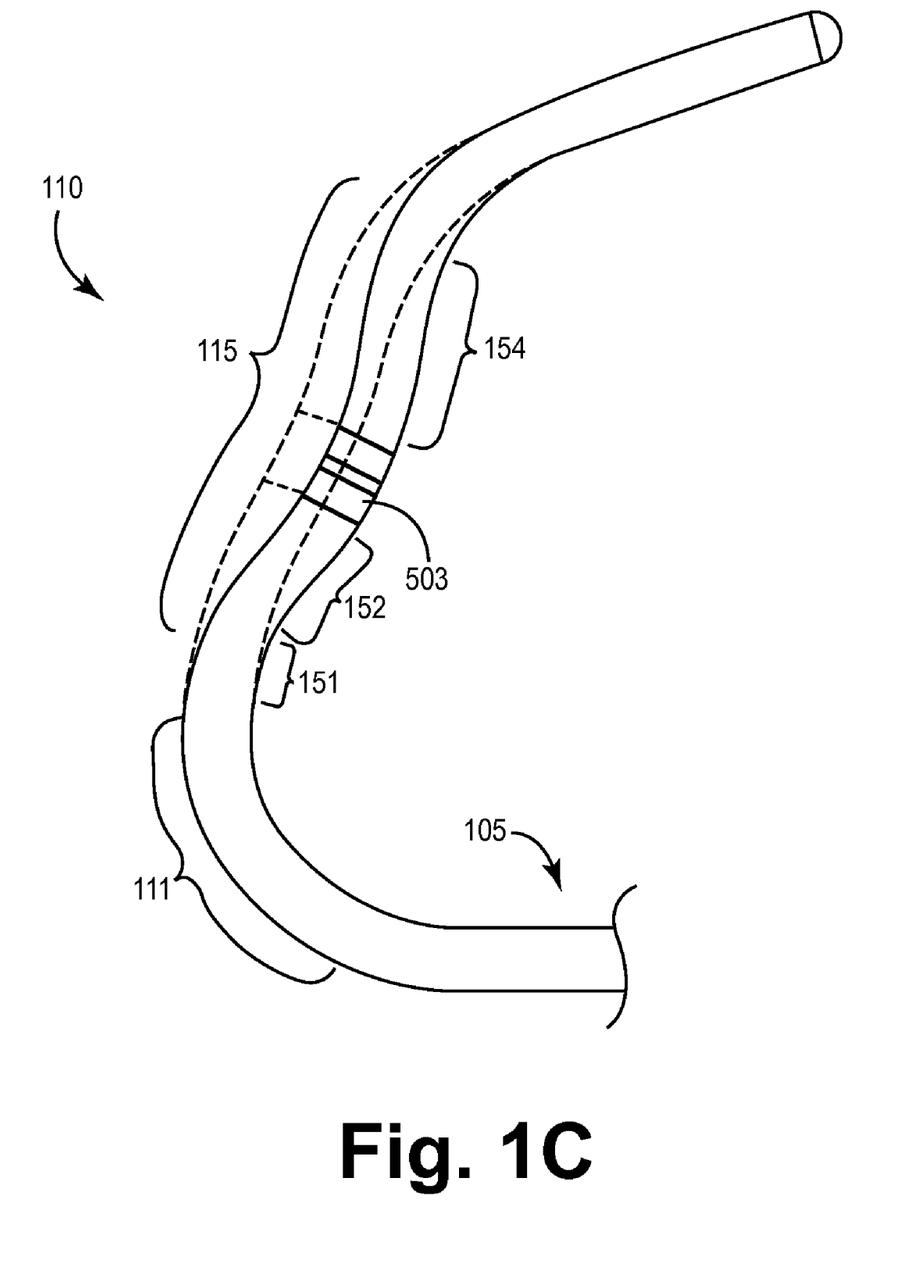
FIG. 1C is a schematic representation of the distal section, from FIG. 1B, in a deformed state.

With reference to FIG. 1C, it may be appreciated that a stiffness of portion 154 of approximately straight distal segment 115 is also less than that of portion 153, in order to allow both portions 152 and portion 154, to bend to as illustrated, further improving contact between electrode 503 and the inner wall of the coronary sinus. According to some embodiments, the stiffness of portion 154 is also less than that of portion 152, for example, being achieved by means of a reduced outer diameter. FIG. 1B further illustrates a stiffening member 501, for example, formed by a tube of 55D durometer, or 80A durometer, polyurethane having an inner diameter of approximately 0.055 inch and an outer diameter of approximately 0.065 inch, extending from a proximal end 557 thereof to a distal end 559 thereof, and about both pre-formed arcuate segment 111 and portion 151 of approximately straight distal segment 115, so that, according to some embodiments, a stiffness of portion 151 is approximately equal to a stiffness of pre-formed arcuate segment 111. Proximal end 557 of stiffening member 501 is shown being located in proximity to a transition from proximal section 105 to pre-formed arcuate segment 111, and distal end 559 of stiffening member 501, in proximity to portion 152 of segment 115; a length of stiffening member 501 may be approximately 0.6 inch. According to exemplary embodiments of the present invention, a length of portion 151 is between approximately 0.11 inch and approximately 0.15 inch, a length of portion 152 is between approximately 0.05 inch and approximately 0.1 inch, a length of portion 153 is between approximately 0.1 inch and approximately 0.16 inch, and a length of portion 154 is between approximately 0.18 inch and approximately 0.22 inch.

Figure 2:
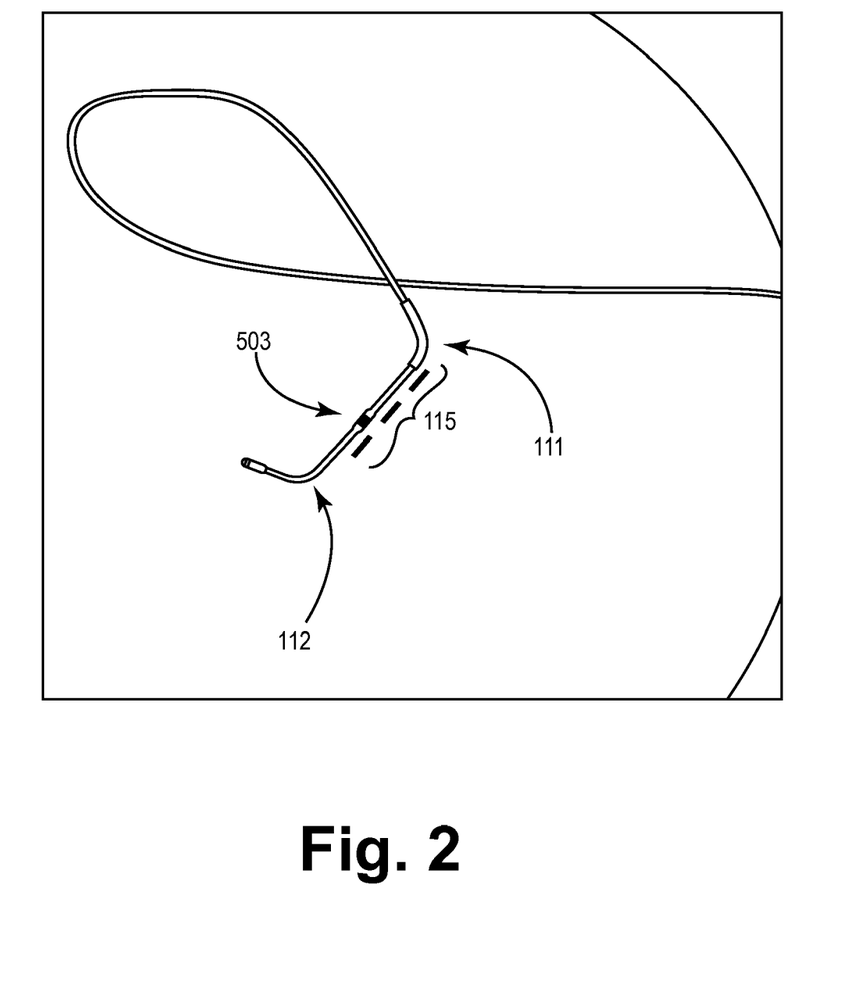
FIG. 2 presents a portion of a fluoroscopic image of an implanted lead, which was constructed according to an embodiment of the present invention.

FIG. 2 presents a portion of a fluoroscopic image of a lead implanted in a coronary vein, which lead includes a distal section similar to distal section 110, described above for lead 10. Those skilled in the art will appreciate, from FIG. 2, how the curvature of a coronary vein, in which lead 10 is implanted, can open up distal section 110, thereby forcing segment 115 in the direction indicated by arrow A of FIG. 1B. With reference to FIG. 2, the buckled contour of segment 115, previously shown in FIG. 1C, can also be seen. The dashed lines in FIGS. 1C and 2 illustrate the approximately straight contour of segment 115 that would be maintained, when segment 115 is forced in the direction of arrow A, were it not for the stiffness of portion 152 being less than that of bordering portions 151 and 153. If segment 115 does not buckle, electrode 503 may be approximately centered within the surrounding tissue of the vein wall, and, if the vein has a larger inner diameter than electrode 503, electrode 503 may not contact the surrounding tissue; if electrode 503 is employed for pacing, the lack of contact may prevent pacing capture or cause higher capture thresholds that can reduce a longevity of the pacing system including electrode 503. According to preferred embodiments of the present invention, electrode 503 is a ring electrode having a diameter between approximately 1.3 mm and approximately 1.8 mm, while a typical range of coronary vein inner diameters, in proximity to the base of the heart (a preferred location for left ventricular pacing), is from approximately 3.5 mm to approximately 5.5 mm. Thus, it may be appreciated that a buckling of segment 115, for example, as is illustrated in FIGS. 1C and 2, may be necessary to bring electrode 503 into contact with the surrounding tissue at a typical implant site, within a coronary vein, for left ventricular pacing.

Figure 3A:
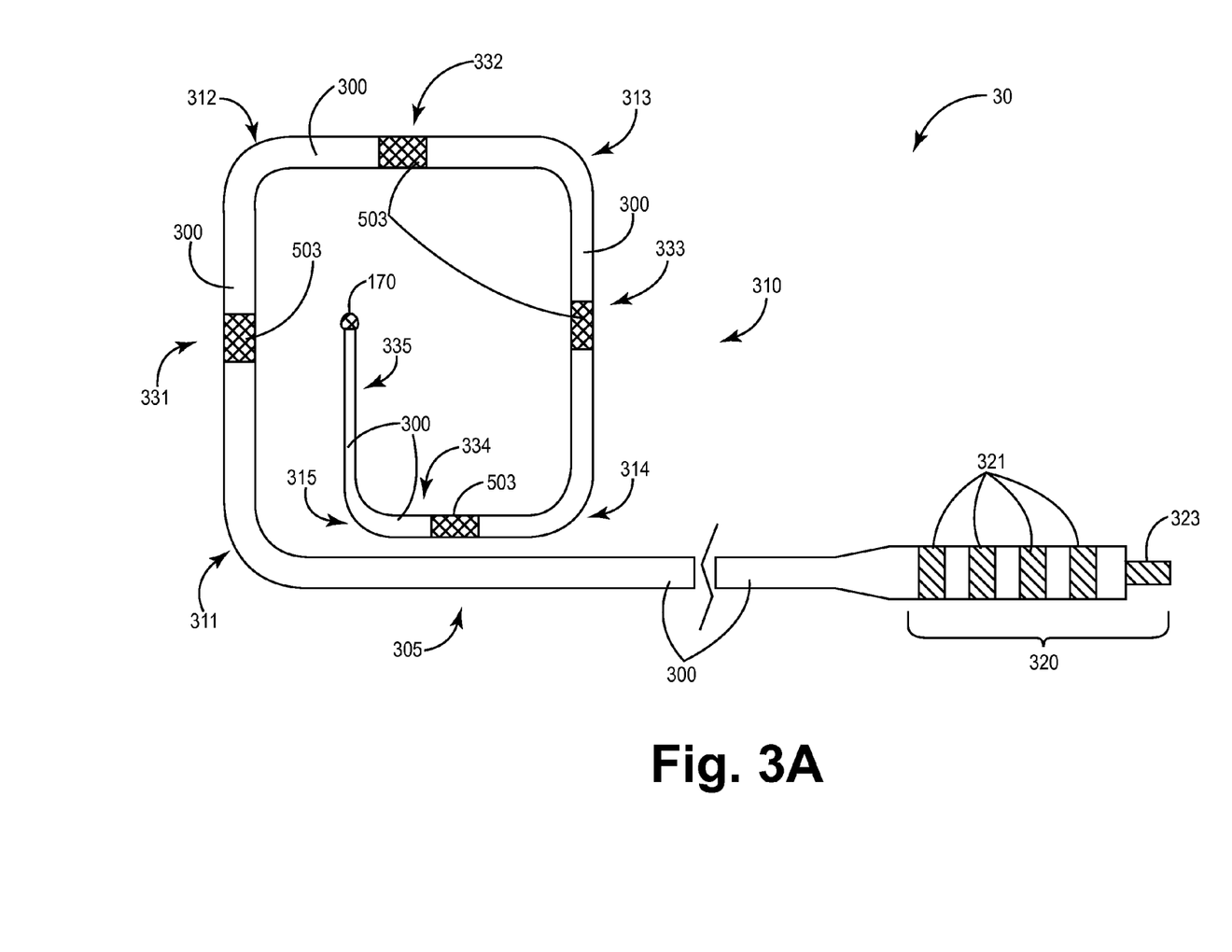
FIG. 3A is a plan view of an implantable medical electrical lead, according to some alternate embodiments of the present invention.
Figure 3B:
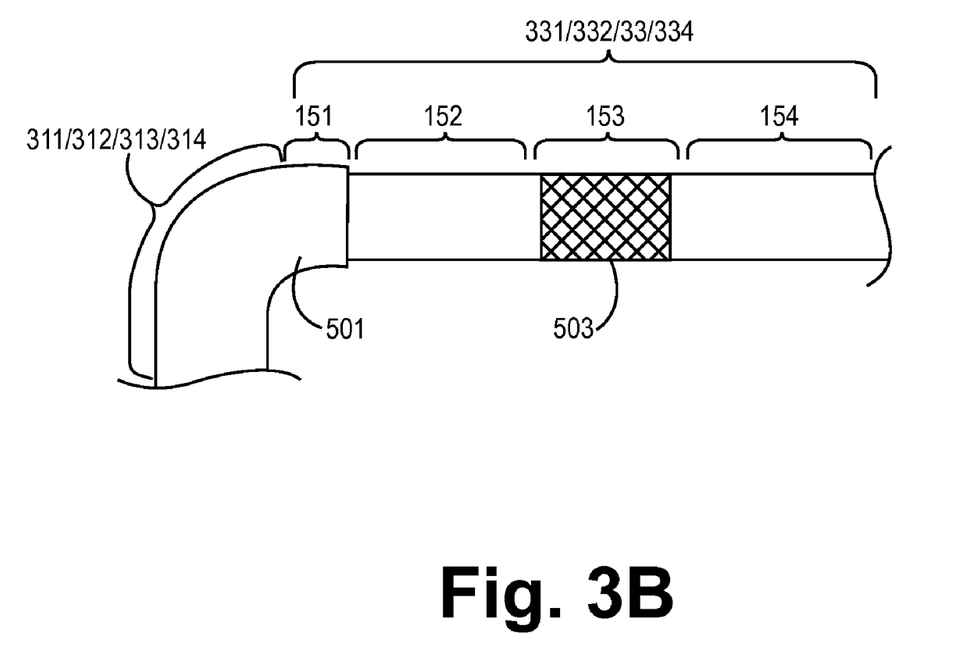
FIG. 3B is an enlarged view of a representative segment of a distal section of the lead shown in FIG. 3A, according to some embodiments.

Turning now to FIGS. 3A-B, an exemplary alternate configuration for a lead body will be described in order to demonstrate the variety of lead body configurations that can incorporate aspects of the present invention. FIG. 3A is a plan view of an implantable medical electrical lead 30, according to some alternate embodiments; and FIG. 3B is an enlarged view of representative segments, according to some aspects of the present invention, which may be incorporated into lead 30.

Like lead body 100 of lead 10, a lead body 300 of lead 30 is formed by a plurality of isolated conductors, and FIG. 3A illustrates lead body 300 including an approximately straight proximal section 305, extending distally from a connector terminal 320 of lead 30, and a distal section 310 extending distally from proximal section 305. FIG. 3A further illustrates distal section 310, like distal section 110, including a pair of pre-formed arcuate segments 311, 312 between which an approximately straight segment 331 extends, but distal section 310, unlike distal section 110, further includes pre-formed arcuate sections 313, 314, 315, respectively, an approximately straight segment 332, which extends between pre-formed arcuate segments 312 and 313, an approximately straight segment 333, which extends between pre-formed arcuate segments 313 and 314, an approximately straight segment 334, which extends between pre-formed arcuate segments 314 and 315, and an approximately straight segment 335, which extends distally from pre-formed arcuate segment 315 to distal tip electrode 170.

According to the illustrated embodiment, a plurality of electrodes 503 are coupled to lead body 300, each electrode 503 to one of approximately straight segments 331, 332, 333, 334 of distal section 310. Those skilled in the art will appreciate each electrode 503 may be coupled to a corresponding contact ring 321 of connector terminal 320, and distal tip electrode 170 to a contact pin 323 of connector terminal 320, via a corresponding isolated conductor of the plurality of conductors forming lead body 300. Preferably, a stiffness of each successive pre-formed arcuate segment 311, 312, 313, 314, and an average stiffness along each successive straight segment 331, 332, 333, 334, 335, decrease from proximal section 305 to tip electrode 170, in order to facilitate the pushing and tracking of lead 310 through tortuous sections of a venous anatomy. Such a decline in stiffness, from proximal to distal, may be accomplished by a gradually tapering diameter, for example, as illustrated in FIG. 3A. Any or all of pre-formed arcuate segments 311, 312, 313, 314, 315 may bend out of plane to lend another dimension to distal section 310, according to some embodiments.

According to some preferred embodiments of the present invention, one or all of approximately straight segments 331, 332, 333, 334 may be tailored to buckle in the manner previously described for segment 115 of lead 10. FIG. 3B is an enlarged view of a representative approximately straight segment 331/332/333/334, of distal section 310 of lead body 300, according to these embodiments. FIG. 3B illustrates approximately straight segment 331/332/333/334 including portions 151, 152, 153, 154 as previously described for segment 115 of distal section 110 of lead 10. FIG. 3B further illustrates stiffening member 501 extending over a representative pre-formed arcuate segment 311/312/313/314, from which segment 331/332/333/334 extends distally, and over adjacent portion 151 of segment 331/332/333/334. According to the illustrated embodiment, member 501 imparts an added stiffness to portion 151, and portion 152 is less stiff than both portions 151 and 153 to preferentially bend, as previously described for distal section 110 of lead 10, when the corresponding curvature of distal section 310 of lead 30 is opened up.

In the foregoing detailed description, the invention has been described with reference to specific embodiments. However, it may be appreciated that various modifications and changes can be made without departing from the scope of the invention as set forth in the appended claims.

We claim:

1. An implantable lead comprising a proximal connector, an elongate lead body extending distally therefrom, and an electrode, the lead body comprising:
   an approximately straight proximal section extending distally from the connector; and
   a distal section extending distally to the proximal section, the distal section comprising:
   a pair of pre-formed arcuate segments; and
   an approximately straight segment extending between the pair of pre-formed arcuate segments and including a first portion extending from a first of the pair of pre-formed arcuate segments and a second portion extending from the first portion;
   the first portion having a first stiffness that is less than the stiffness of the first of the pair of pre-formed arcuate segments, the second portion having a second stiffness that is greater than the first stiffness and the first electrode located along the second portion.

2. The lead of claim 1, wherein the first of the pair of pre-formed arcuate segments of the distal section is adjacent to and extends from the proximal section and the first portion of the approximately straight segment extends distal to the first of the pair of pre-formed arcuate segments.

3. The lead of claim 2, wherein the first arcuate segment is free of electrodes.

4. The lead of claim 1, wherein the first arcuate segment is free of electrodes.

5. The lead of claim 1 wherein the approximately straight segment comprises a third portion extending from the second portion and the third portion has a stiffness that is less than the second stiffness.

6. The lead of claim 5, wherein the third stiffness is less than the first stiffness.

7. The lead of claim 1, wherein the electrode extends about a circumference of the second portion of the approximately straight segment of the distal section and has an outer diameter between approximately 1.3 mm and approximately 1.8 mm.

8. The lead of claim 1, further comprising a stiffening member extending about the first segment of the pair of pre-formed arcuate segments.

9. The lead of claim 1 further comprising a distal tip electrode terminating the distal section.

10. The lead of claim 1, wherein the pair of arcuate segments have curvatures of between 45 and 90 degrees.

11. A method of stimulating a patient's heart comprising:
    inserting into the patient's coronary vein an implantable lead comprising a proximal connector, an elongate lead body extending distally therefrom, and an electrode, the lead body comprising:
    an approximately straight proximal section extending distally from the connector; and
    a distal section extending distally to the proximal section, the distal section comprising:

a pair of pre-formed arcuate segments; and a first approximately straight segment extending between the pair of pre-formed arcuate segments and including a first portion extending from a first of the pair of pre-formed arcuate segments and a second portion extending from the first portion;

the first portion having a first stiffness that is less than the stiffness of the first of the pair of pre-formed arcuate segments, the second portion having a second stiffness that is greater than the first stiffness and the first electrode located along the second portion;

wherein the lead is inserted so that the first arcuate segment bears against the wall of the coronary vein and the first portion bends in response thereto to allow the electrode to contact an inner wall of the coronary vein; and applying stimulus pulses using the electrode.

12. The method of claim 11, wherein first of the pair of pre-formed arcuate segments of the distal section of the inserted the lead is adjacent to and extends from the proximal section and the first portion of the first approximately straight segment extends distal to the first of the pair of pre-formed arcuate segments.

13. The method of claim 12, wherein the first arcuate segment of the inserted the lead is free of electrodes.

14. The method of claim 11, wherein the first arcuate segment of the inserted the lead is free of electrodes.

15. The method claim 11 wherein the first approximately straight segment of the inserted the lead comprises a third portion extending from the second portion and the third portion has a stiffness that is less than the second stiffness.

16. The method of claim 15, wherein the third stiffness of the inserted the lead is less than the first stiffness.

17. The method of claim 16, wherein the electrode of the inserted the lead extends about a circumference of the second portion of the approximately straight segment of the distal section and has an outer diameter between approximately 1.3 mm and approximately 1.8 mm.

18. The method of claim 11, wherein the inserted the lead further comprises a stiffening member extending about the first segment of the pair of pre-formed arcuate segments.

19. The method of claim 11 wherein the inserted the lead further comprises a distal tip electrode terminating the distal section.

20. The method of claim 11 wherein the pair of arcuate segments of the inserted lead have curvatures of between 45 and 90 degrees.

* * * * *

UNITED STATES PATENT AND TRADEMARK OFFICE
CERTIFICATE OF CORRECTION

| | |
|---|---|
| PATENT NO. | : 8,041,434 B2 |
| APPLICATION NO. | : 12/413176 |
| DATED | : October 18, 2011 |
| INVENTOR(S) | : William J. Clemens et al. |

It is certified that error appears in the above-identified patent and that said Letters Patent is hereby corrected as shown below:

In the Claims:

Col. 8, line 3, delete "method claim 11 wherein" and insert in place thereof -- method of claim 11, wherein --;

Signed and Sealed this
Thirtieth Day of April, 2013

Teresa Stanek Rea
*Acting Director of the United States Patent and Trademark Office*